(12) United States Patent
Gale et al.

(10) Patent No.: US 8,172,897 B2
(45) Date of Patent: May 8, 2012

(54) POLYMER AND METAL COMPOSITE IMPLANTABLE MEDICAL DEVICES

(75) Inventors: David C. Gale, San Jose, CA (US); Bin Huang, Pleasanton, CA (US); John M Capek, Los Gatos, CA (US); John Y. Yan, Los Gatos, CA (US); Houdin Dehnad, El Granada, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1297 days.

(21) Appl. No.: 10/880,025

(22) Filed: Jun. 28, 2004
(Under 37 CFR 1.47)

(65) Prior Publication Data
US 2005/0209680 A1 Sep. 22, 2005

Related U.S. Application Data

(60) Continuation-in-part of application No. 10/767,296, filed on Jan. 28, 2004, now Pat. No. 7,699,890, which is a division of application No. 10/235,033, filed on Sep. 3, 2002, now Pat. No. 6,723,120, which is a continuation of application No. 09/797,313, filed on Mar. 1, 2001, now abandoned, which is a division of application No. 08/837,993, filed on Apr. 15, 1997, now Pat. No. 6,240,616.

(51) Int. Cl.
*A61F 2/06* (2006.01)
(52) U.S. Cl. ........................ 623/1.38; 623/1.42; 623/1.44
(58) Field of Classification Search ................ 623/1.15, 623/1.12, 1.13, 1.14, 1.38, 1.4, 1.42, 1.44, 623/1.45, 1.46; 427/2.1
See application file for complete search history.

(56) References Cited

U.S. PATENT DOCUMENTS

| | | | |
|---|---|---|---|
| 3,687,135 A | 8/1972 | Stroganov et al. | |
| 3,839,743 A | 10/1974 | Schwarcz | |
| 3,855,638 A | 12/1974 | Pilliar | |
| 3,900,632 A | 8/1975 | Robinson | |

(Continued)

FOREIGN PATENT DOCUMENTS
DE 44 07 079 9/1994
(Continued)

OTHER PUBLICATIONS

U.S. Appl. No. 10/317,435, filed Dec. 11, 2002, Hossainy et al.
(Continued)

*Primary Examiner* — Corrine M McDermott
*Assistant Examiner* — Jing Rui Ou
(74) *Attorney, Agent, or Firm* — Squire Sanders (US) LLP (57) ABSTRACT

A device and a method of manufacturing an implantable medical device, such as a stent, are described herein. The device includes a metallic region composed of a bioerodable metal and a polymer region composed of a biodegradable polymer contacting the metallic region. The metallic region may erode at a different rate when exposed to bodily fluids than the polymer region when exposed to bodily fluids. In certain embodiments, the polymer region is an outer layer and the metallic region is an inner layer of the device. A further aspect of the invention includes device and a method of manufacturing the device that includes a mixture of a biodegradable polymer and bioerodable metallic particles. The mixture may be used to fabricate an implantable medical device or to coat an implantable medical device. In some embodiments, the metallic particles are metallic nanoparticles.

27 Claims, 3 Drawing Sheets

U.S. PATENT DOCUMENTS

| | | |
|---|---|---|
| 4,101,984 A | 7/1978 | MacGregor |
| 4,104,410 A | 8/1978 | Malecki |
| 4,110,497 A | 8/1978 | Hoel |
| 4,321,711 A | 3/1982 | Mano |
| 4,346,028 A | 8/1982 | Griffith |
| 4,355,426 A | 10/1982 | MacGregor |
| 4,374,669 A | 2/1983 | MacGregor |
| 4,405,319 A | 9/1983 | Cosentino |
| 4,458,366 A | 7/1984 | MacGregor |
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |
| 4,693,721 A | 9/1987 | Ducheyne |
| 4,718,907 A | 1/1988 | Karwoski et al. |
| 4,722,335 A | 2/1988 | Vilasi |
| 4,723,549 A | 2/1988 | Wholey et al. |
| 4,729,871 A | 3/1988 | Morimoto |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,902,289 A | 2/1990 | Yannas |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,078,736 A | 1/1992 | Behl |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,171,262 A | 12/1992 | MacGregor |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,370,682 A | 12/1994 | Schmitt |
| 5,370,684 A | 12/1994 | Vallana et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,419,760 A | 5/1995 | Narciso, Jr. |
| 5,423,885 A | 6/1995 | Williams |
| 5,433,909 A | 7/1995 | Marakos et al. |
| 5,437,834 A | 8/1995 | Okimatsu et al. |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. |
| 5,477,864 A | 12/1995 | Davidson |
| 5,492,768 A | 2/1996 | Okimatsu et al. |
| 5,502,158 A | 3/1996 | Sinclair et al. |
| 5,514,379 A | 5/1996 | Weissleder et al. |
| 5,518,730 A | 5/1996 | Fuisz |
| 5,522,894 A | 6/1996 | Draenert |
| 5,527,337 A | 6/1996 | Stack et al. |
| 5,540,712 A | 7/1996 | Kleshinski et al. |
| 5,545,408 A | 8/1996 | Trigg et al. |
| 5,554,120 A | 9/1996 | Chen et al. |
| 5,556,413 A | 9/1996 | Lam |
| 5,571,187 A | 11/1996 | Devanathan |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,693 A | 2/1997 | Seare, Jr. |
| 5,605,696 A | 2/1997 | Eury et al. |
| 5,607,442 A | 3/1997 | Fischell et al. |
| 5,607,463 A | 3/1997 | Schwartz et al. |
| 5,607,467 A | 3/1997 | Froix |
| 5,618,299 A | 4/1997 | Khosravi et al. |
| 5,624,411 A | 4/1997 | Tuch |
| 5,629,077 A | 5/1997 | Turnlund et al. |
| 5,630,840 A | 5/1997 | Mayer |
| 5,631,135 A | 5/1997 | Gryaznov et al. |
| 5,632,771 A | 5/1997 | Boatman et al. |
| 5,632,779 A | 5/1997 | Davidson |
| 5,632,840 A | 5/1997 | Campbell |
| 5,637,113 A | 6/1997 | Tartaglia et al. |
| 5,641,443 A | 6/1997 | Calcote et al. |
| 5,649,977 A | 7/1997 | Campbell |
| 5,667,767 A | 9/1997 | Greff et al. |
| 5,667,796 A | 9/1997 | Otten |
| 5,670,558 A | 9/1997 | Onishi et al. |
| 5,693,085 A | 12/1997 | Buirge et al. |
| 5,697,967 A | 12/1997 | Dinh et al. |
| 5,700,286 A | 12/1997 | Tartaglia et al. |
| 5,707,385 A | 1/1998 | Williams |
| 5,711,763 A | 1/1998 | Nonami et al. |
| 5,713,949 A | 2/1998 | Jayaraman |
| 5,716,981 A | 2/1998 | Hunter et al. |
| 5,725,549 A | 3/1998 | Lam |
| 5,725,567 A | 3/1998 | Wolff et al. |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,746,691 A | 5/1998 | Frantzen |
| 5,755,771 A | 5/1998 | Penn et al. |
| 5,756,457 A | 5/1998 | Wang et al. |
| 5,756,476 A | 5/1998 | Epstein et al. |
| 5,759,192 A | 6/1998 | Saunders |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,769,884 A | 6/1998 | Solovay |
| 5,780,807 A | 7/1998 | Saunders |
| 5,788,558 A | 8/1998 | Klein |
| 5,800,512 A | 9/1998 | Lentz et al. |

| Patent No. | Date | Inventor(s) |
|---|---|---|
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,843,172 A | 12/1998 | Yan |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,856,814 A | 1/1999 | Yagyu |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,398 A | 3/1999 | Swarts et al. |
| 5,879,713 A | 3/1999 | Roth et al. |
| 5,888,533 A | 3/1999 | Dunn |
| 5,891,192 A | 4/1999 | Murayama et al. |
| 5,897,955 A | 4/1999 | Drumheller |
| 5,906,759 A | 5/1999 | Richter |
| 5,914,182 A | 6/1999 | Drumheller |
| 5,916,584 A | 6/1999 | O'Donoghue |
| 5,916,870 A | 6/1999 | Lee et al. |
| 5,922,005 A | 7/1999 | Richter et al. |
| 5,928,279 A | 7/1999 | Shannon et al. |
| 5,942,209 A | 8/1999 | Leavitt et al. |
| 5,945,029 A | 8/1999 | Scholz et al. |
| 5,948,428 A | 9/1999 | Lee et al. |
| 5,954,744 A | 9/1999 | Phan et al. |
| 5,957,975 A | 9/1999 | Lafont et al. |
| 5,965,720 A | 10/1999 | Gryaznov et al. |
| 5,971,954 A | 10/1999 | Conway et al. |
| 5,972,027 A | 10/1999 | Johnson |
| 5,976,182 A | 11/1999 | Cox |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,986,169 A | 11/1999 | Gjunter |
| 5,997,468 A | 12/1999 | Wolff et al. |
| 6,010,445 A | 1/2000 | Armini et al. |
| 6,010,529 A | 1/2000 | Herweck et al. |
| 6,015,541 A | 1/2000 | Greff et al. |
| 6,027,779 A | 2/2000 | Campbell et al. |
| 6,033,582 A | 3/2000 | Lee et al. |
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |
| 6,066,156 A | 5/2000 | Yan |
| 6,071,266 A | 6/2000 | Kelley |
| 6,074,659 A | 6/2000 | Kunz et al. |
| 6,080,177 A | 6/2000 | Igaki et al. |
| 6,080,488 A | 6/2000 | Hostettler et al. |
| 6,083,258 A | 7/2000 | Yadav |
| 6,093,463 A | 7/2000 | Thakrar |
| 6,095,817 A | 8/2000 | Wagner et al. |
| 6,096,070 A | 8/2000 | Ragheb et al. |
| 6,096,525 A | 8/2000 | Patnaik |
| 6,099,562 A | 8/2000 | Ding et al. |
| 6,103,230 A | 8/2000 | Billiar et al. |
| 6,107,416 A | 8/2000 | Patnaik et al. |
| 6,110,188 A | 8/2000 | Narciso, Jr. |
| 6,113,629 A | 9/2000 | Ken |
| 6,117,979 A | 9/2000 | Hendriks et al. |
| 6,120,536 A | 9/2000 | Ding et al. |
| 6,120,904 A | 9/2000 | Hostettler et al. |
| 6,121,027 A | 9/2000 | Clapper et al. |
| 6,125,523 A | 10/2000 | Brown et al. |
| 6,127,173 A | 10/2000 | Eckstein et al. |
| 6,129,761 A | 10/2000 | Hubbell |
| 6,129,928 A | 10/2000 | Sarangapani et al. |
| 6,143,370 A | 11/2000 | Panagiotou et al. |
| 6,150,630 A | 11/2000 | Perry et al. |
| 6,153,252 A | 11/2000 | Hossainy et al. |
| 4,776,337 A | 12/2000 | Palmaz |
| 6,159,951 A | 12/2000 | Karpeisky et al. |
| 6,160,084 A | 12/2000 | Langer et al. |
| 6,165,210 A | 12/2000 | Lau et al. |
| 6,165,212 A | 12/2000 | Dereume et al. |
| 6,166,130 A | 12/2000 | Rhee et al. |
| 6,169,170 B1 | 1/2001 | Gryaznov et al. |
| 6,171,609 B1 | 1/2001 | Kunz |
| 6,174,330 B1 | 1/2001 | Stinson |
| 6,177,523 B1 | 1/2001 | Reich et al. |
| 6,183,505 B1 | 2/2001 | Mohn, Jr. et al. |
| 6,187,045 B1 | 2/2001 | Fehring et al. |
| 6,210,715 B1 | 4/2001 | Starling et al. |
| 6,224,626 B1 | 5/2001 | Steinke |
| 6,228,845 B1 | 5/2001 | Donovan et al. |
| 6,240,616 B1 | 6/2001 | Yan |
| 6,245,076 B1 | 6/2001 | Yan |
| 6,245,103 B1 | 6/2001 | Stinson |
| 6,248,344 B1 | 6/2001 | Ylanen et al. |
| 6,251,135 B1 | 6/2001 | Stinson et al. |
| 6,251,142 B1 | 6/2001 | Bernacca et al. |
| 6,273,913 B1 | 8/2001 | Wright et al. |
| 6,281,262 B1 | 8/2001 | Shikinami |
| 6,284,333 B1 | 9/2001 | Wang et al. |
| 6,287,332 B1 | 9/2001 | Bolz et al. |
| 6,287,337 B1 | 9/2001 | Martakos et al. |
| 6,290,721 B1 | 9/2001 | Heath |
| 6,293,966 B1 | 9/2001 | Frantzen |
| 6,303,901 B1 | 10/2001 | Perry et al. |
| 6,312,459 B1 | 11/2001 | Huang et al. |
| 6,327,772 B1 | 12/2001 | Zadno-Azizi et al. |
| 6,338,739 B1 * | 1/2002 | Datta et al. .................. 623/1.15 |
| 6,375,826 B1 | 4/2002 | Wang et al. |
| 6,379,381 B1 | 4/2002 | Hossainy et al. |
| 6,387,121 B1 | 5/2002 | Alt |
| 6,388,043 B1 | 5/2002 | Langer et al. |
| 6,395,326 B1 | 5/2002 | Castro et al. |
| 6,409,761 B1 | 6/2002 | Jang |
| 6,423,092 B2 | 7/2002 | Datta et al. |
| 6,461,632 B1 | 10/2002 | Gogolewski |
| 6,464,720 B2 | 10/2002 | Boatman et al. |
| 6,479,565 B1 | 11/2002 | Stanley |
| 6,485,512 B1 | 11/2002 | Cheng |
| 6,492,615 B1 | 12/2002 | Flanagan |
| 6,494,908 B1 | 12/2002 | Huxel et al. |
| 6,495,156 B2 | 12/2002 | Wenz et al. |
| 6,511,748 B1 | 1/2003 | Barrows |
| 6,517,888 B1 | 2/2003 | Weber |
| 6,527,801 B1 | 3/2003 | Dutta |
| 6,537,589 B1 | 3/2003 | Chae et al. |
| 6,539,607 B1 | 4/2003 | Fehring et al. |
| 6,540,777 B2 | 4/2003 | Stenzel |
| 6,554,854 B1 | 4/2003 | Flanagan |
| 6,565,599 B1 | 5/2003 | Hong et al. |
| 6,569,191 B1 | 5/2003 | Hogan |
| 6,569,193 B1 | 5/2003 | Cox et al. |
| 6,572,672 B2 | 6/2003 | Yadav et al. |
| 6,574,851 B1 | 6/2003 | Mirizzi |
| 6,585,755 B2 | 7/2003 | Jackson et al. |
| 6,589,286 B1 * | 7/2003 | Litner .......................... 623/23.7 |
| 6,592,614 B2 | 7/2003 | Lenker et al. |
| 6,592,617 B2 | 7/2003 | Thompson |
| 6,610,087 B1 | 8/2003 | Zarbatany et al. |
| 6,613,072 B2 | 9/2003 | Lau et al. |
| 6,626,939 B1 | 9/2003 | Burnside et al. |
| 6,635,269 B1 | 10/2003 | Jennissen |
| 6,645,243 B2 | 11/2003 | Vallana et al. |
| 6,656,162 B2 | 12/2003 | Santini, Jr. et al. |

| | | | |
|---|---|---|---|
| 6,664,335 B2 | 12/2003 | Krishnan | |
| 6,666,214 B2 | 12/2003 | Canham | |
| 6,667,049 B2 | 12/2003 | Janas et al. | |
| 6,669,723 B2 | 12/2003 | Killion et al. | |
| 6,676,697 B1 | 1/2004 | Richter | |
| 6,679,980 B1 | 1/2004 | Andreacchi | |
| 6,689,375 B1 | 2/2004 | Wahlig et al. | |
| 6,695,920 B1 | 2/2004 | Pacetti et al. | |
| 6,706,273 B1 | 3/2004 | Roessler | |
| 6,709,379 B1 | 3/2004 | Brandau et al. | |
| 6,719,934 B2 | 4/2004 | Stinson | |
| 6,719,989 B1 | 4/2004 | Matsushima et al. | |
| 6,720,402 B2 | 4/2004 | Langer et al. | |
| 6,723,120 B2 | 4/2004 | Yan | |
| 6,746,773 B2 | 6/2004 | Llanos et al. | |
| 6,752,826 B2 | 6/2004 | Holloway et al. | |
| 6,753,007 B2 | 6/2004 | Haggard et al. | |
| 6,764,505 B1 | 7/2004 | Hossainy et al. | |
| 6,818,063 B1 | 11/2004 | Kerrigan | |
| 6,846,323 B2 | 1/2005 | Yip et al. | |
| 6,867,248 B1 | 3/2005 | Martin et al. | |
| 6,981,987 B2 * | 1/2006 | Huxel et al. | 623/1.22 |
| 7,011,678 B2 * | 3/2006 | Tenerz et al. | 623/1.15 |
| 7,163,562 B2 * | 1/2007 | Datta et al. | 623/23.7 |
| 7,166,134 B2 * | 1/2007 | Datta et al. | 623/23.7 |
| 2001/0044652 A1 | 11/2001 | Moore | |
| 2002/0002399 A1 | 1/2002 | Huxel et al. | |
| 2002/0004060 A1 | 1/2002 | Heublein et al. | |
| 2002/0004101 A1 | 1/2002 | Ding et al. | |
| 2002/0038145 A1 | 3/2002 | Jang | |
| 2002/0062148 A1 | 5/2002 | Hart | |
| 2002/0065553 A1 | 5/2002 | Weber | |
| 2002/0082679 A1 | 6/2002 | Sirhan et al. | |
| 2002/0111590 A1 | 8/2002 | Davila et al. | |
| 2002/0116050 A1 | 8/2002 | Kocur | |
| 2002/0138133 A1 | 9/2002 | Lenz et al. | |
| 2002/0161114 A1 | 10/2002 | Gunatillake et al. | |
| 2002/0165601 A1 | 11/2002 | Clerc | |
| 2003/0033001 A1 | 2/2003 | Igaki | |
| 2003/0093107 A1 | 5/2003 | Parsonage et al. | |
| 2003/0100865 A1 | 5/2003 | Santini, Jr. et al. | |
| 2003/0105518 A1 | 6/2003 | Dutta | |
| 2003/0105530 A1 | 6/2003 | Pirhonen | |
| 2003/0153972 A1 | 8/2003 | Helmus | |
| 2003/0171053 A1 | 9/2003 | Sanders | |
| 2003/0187495 A1 | 10/2003 | Cully et al. | |
| 2003/0208259 A1 | 11/2003 | Penhasi | |
| 2003/0209835 A1 | 11/2003 | Chun et al. | |
| 2003/0226833 A1 | 12/2003 | Shapovalov et al. | |
| 2003/0236563 A1 | 12/2003 | Fifer | |
| 2004/0034409 A1 | 2/2004 | Heublein et al. | |
| 2004/0088038 A1 | 5/2004 | Dehnad et al. | |
| 2004/0093077 A1 | 5/2004 | White et al. | |
| 2004/0098095 A1 | 5/2004 | Burnside et al. | |
| 2004/0111149 A1 | 6/2004 | Stinson | |
| 2004/0127970 A1 | 7/2004 | Saunders et al. | |
| 2004/0143317 A1 | 7/2004 | Stinson et al. | |
| 2004/0167610 A1 | 8/2004 | Fleming, III | |
| 2005/0209680 A1 | 9/2005 | Gale et al. | |
| 2005/0261760 A1 | 11/2005 | Weber | |
| 2006/0229711 A1 | 10/2006 | Yan et al. | |
| 2006/0271168 A1 | 11/2006 | Kleine et al. | |

FOREIGN PATENT DOCUMENTS

| | | |
|---|---|---|
| DE | 197 31 021 | 1/1999 |
| DE | 198 56 983 | 12/1999 |
| DE | 103 57 747 | 1/2005 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 687 008 | 12/1995 |
| EP | 0 709 068 | 5/1996 |
| EP | 0 970 711 | 1/2000 |
| EP | 1 362 603 | 11/2003 |
| GB | 2 247 696 | 3/1992 |
| JP | 63-160645 | 7/1988 |
| JP | 3-14516 | 1/1991 |
| JP | 4-215768 | 8/1992 |
| JP | 8-33718 | 2/1996 |
| JP | 8-213026 | 8/1996 |
| JP | 9-85028 | 3/1997 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/13268 | 6/1994 |
| WO | WO 94/21196 | 9/1994 |
| WO | WO 95/11817 | 5/1995 |
| WO | WO 95/29647 | 11/1995 |
| WO | WO 96/28115 | 9/1996 |
| WO | WO 98/04415 | 2/1998 |
| WO | WO 98/18408 * | 5/1998 |
| WO | WO 98/23228 | 6/1998 |
| WO | WO 98/56312 | 12/1998 |
| WO | WO 99/03515 | 1/1999 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 03/63733 | 8/2003 |
| WO | WO 2004/023985 | 3/2004 |

OTHER PUBLICATIONS

Anonymous, *Bioabsorbable stent mounted on a catheter having optical coherence tomography capabilities*, Research Disclosure, Sep. 2004, pp. 1159-1162.

Ansari, *Tubal Reanastomosis Using Absorbable Stent*, International Journal of Fertility, vol. 23, No. 4, pp. 242-243 (1978).

Ansari, *End-to-end tubal anastomosis using an absorbable stent*, Fertility and Sterility, vol. 32(2), pp. 197-201 (Aug. 1979).

Bull, *Palylene Coating for Medical Applications*, Medical Product Manufacturing News, 1 pg. (Mar. 1993).

Casper et al., *Fiber-Reinforced Absorbable Composite for Orthopedic Surgery*, Polymeric Materials Science and Engineering, 53:497-501 (1985).

Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).

Devanathan et al., *Polymeric Conformal Coatings for Implantable Electronic Devices*, IEEE Transactions on Biomedical Engineering, vol. BME-27(11), pp. 671-675 (1980).

Elbert et al., *Conjugate Addition Reactions Combined with Free-Radical Cross-Linking for the Design of Materials for Tissue Engineering*, Biomacromolecules 2, pp. 430-441 (2001).

Feng-Chun et al., *Assessment of Tissue Blood Flow Following Small Artery Welding with an Intraluminal Dissolvable Stent*, Microsurgery, vol. 19(3), pp. 148-152 (1999).

Hahn et al., *Biocompatibility of Glow-Discharge-Polymerized Films and Vacuum-Deposited Parylene*, J Applied Polymer Sci, 38, pp. 55-64 (1984).

Hahn et al., *Glow Discharge Polymers as Coatings for Implanted Devices*, ISA, pp. 109-111 (1981).

Kelley et al., *Totally Resorbable High-Strength Composite Material*, Advances in Biomedical Polymers, 35, pp. 75-85 (1987).

Kubies et al., *Microdomain Structure in polylactide-block-poly(ethylene oxide) copolymer films*, Biomaterials 21, pp. 529-536 (2000).

Kutryk et al., *Coronary Stenting: Current Perspectives*, a companion to the Handbook of Coronary Stents 16 pgs. (1999).

Lambert et al., *Localized Arterial Wall Drug Delivery From a Polymer-Coated Removable Metallic Stent*, Circulation 90(2):1003-1011 (Aug. 1994).

Martin et al., *Enhancing the biological activity of immobilized osteopontin using a type-1 collagen affinity coating*, J. Biomed. Mater Res 70A, pp. 10-19 (2004).

Mauduit et al., *Hydrolytic degradation of films prepared from blends of high and low molecular weight poly(DL-lactic acid)s*, J. Biomed. Mater. Res. v. 30, pp. 201-207 (1996).

Middleton et al., *Synthetic biodegradable polymers as orthopedic devices*, Biomaterials, vol. 21, pp. 2335-2346 (2000).

Muller et al., *Advances in Coronary Angioplasty: Endovascular Stents*, Coron. After. Dis., 1(4), pp. 438-448 (Jul./Aug. 1990).

Nichols et al., *Electrical Insulation of Implantable Devices by Composite Polymer Coatings*, ISA Transactions, 26(4), pp. 15-18 (1987).

Peuster et al., *A novel approach to temporary stenting: degradable cardiovascular stents produced from corrodible metal-results 6-18 months after implantation into New Zealand white rabbits*, Heart 86, pp. 563-569 (2001).

Pietrzak et al., *Bioresorbable implants—practical considerations*, Bone v. 19, No. 1, Supplement Jul. 1996: 109S-119S.

Pietrzak et al., *Bioabsorbable Fixation Devices: Status for the Craniomaxillofacial Surgeon*, J. Craniofaxial Surg. 2, pp. 92-96 (1997).

von Recum et al., *Degradation of polydispersed poly(L-lactic acid) to modulate lactic acid release*, Biomaterials 16, pp. 441-445 (1995).

Redman, *Clinical Experience with Vasovasostomy Utilizing Absorbable Intravasal Stent*, Urology, vol. 20(1), pp. 59-61 (Jul. 1982).

Rust et al., *The Effects of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).

Schatz, *A View of Vascular Stents*, Circulation, 79(2), pp. 445-457 (Feb. 1989).

De Scheerder et al., *Biocompatibility of Polymer-Coated Oversized Metallic Stents Implanted in Normal Porcine Coronary Arteries*, Atherosclerosis 114:105-114 (1995).

Schmidt et al., *Long-Term Implants of Parylene-C Coated Microelectrodes*, Med & Biol Eng & Comp, 26(1), pp. 96-101 (Jan. 1988).

Spagnuolo et al., *Gas 1 is induced by VE-cadherin and vascular endothelial growth factor and inhibits endothelial cell apoptosis*, Blood 103, pp. 3005-3012 (2004).

Tamai et al., *Initial and 6-Month Results of Biodegradable Poly-I-Lactic Acid Coronary Stents in Humans*, Circulation , pp. 399-404 (2000).

Tsui et al., *Biodegradable Polymeric Stents*, Current Interventional Cardiology Reports 3, pp. 10-17 (2001).

Völkel et al., *Targeting of immunoliposomes to endothelial cells using a single—chain Fv fragment directed against human endoglin (CD105)*, Biochemica et Biophysica Acta 1663, pp. 158-166 (2004).

Yau et al. "Modern Size-Exclusion Liquid Chromatography", Wiley-Interscience Publication (1979).

International Search Report for PCT/US2006/025937 filed Jun. 30, 2006, mailed Nov. 9, 2006, 18 pgs.

International Search Report for PCT/US2007/011177, mailed Aug. 11, 2008, 13 pgs.

Feng-Chun et al., *Assessment of Tissue Blood Flow Following Small Artery Welding with an Intraluminal Dissolvable Stent*, Microsurgery, vol. 19(3), pp. 148-152 (1999).

*Properties and Selection: Nonferrous Alloys and Special-Purpose Materials*, taken from: Housh S., Mikucki B. ASM Handbook vol. 2, last udated Oct. 24, 2008, Web Article: http://mq.tripod.com/asm_prop.htm.

Song et al., *Electrodeposition of hydroxyapatite coating on AZ91D magnesium alloy for biomaterial application*, Mat. Let. 62, pp. 3276-3279 (2008).

\* cited by examiner

POLYMER AND METAL COMPOSITE IMPLANTABLE MEDICAL DEVICES

CROSS-REFERENCE

This is a continuation-in-part of application Ser. No. 10/767,296 filed on Jan. 28, 2004, now U.S. Pat. No. 7,699,890 which is a divisional application of application Ser. No. 10/235,033, which was filed on Sep. 3, 2002, now U.S. Pat. No. 6,723,120 which is a continuation of the application Ser. No. 09/797,313, filed on Mar. 1, 2001, now abandoned, which is a division of application Ser. No. 08/837,993, filed on Apr. 15, 1997, and issued Jun. 5, 2001 as U.S. Pat. No. 6,240,616.

BACKGROUND OF THE INVENTION

1. Field of the Invention

This invention relates to polymer and metal composite implantable medical devices, such as stents.

2. Description of the State of the Art

This invention relates to radially expandable endoprostheses which are adapted to be implanted in a bodily lumen. An "endoprosthesis" corresponds to an artificial device that is placed inside the body. A "lumen" refers to a cavity of a tubular organ such as a blood vessel. A stent is an example of an endoprosthesis. Stents are generally cylindrically shaped devices which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty or valvuloplasty) with apparent success.

Stents have been made of many materials including metals and polymers. Polymer materials include both biostable and biodegradable polymer materials. Metallic stents are typically formed from biostable metals. However, bioerodable metal stents have been described. U.S. Pat. No. 6,287,332 B1 to Bolz et al., U.S. Pat. Appl. Pub. No. 2002/0004060 A1 to Heublein et. al. The cylindrical structure of stents is typically composed of a scaffolding that includes a pattern or network of interconnecting structural elements or struts. The scaffolding can be formed from wires, tubes, or planar films or sheets of material rolled into a cylindrical shape. In addition, a medicated stent may be fabricated by coating the surface of either a metallic or polymeric scaffolding with a polymeric carrier. The polymeric carrier can include an active agent or drug. Furthermore, the pattern that makes up the stent allows the stent to be radially expandable and longitudinally flexible. Longitudinal flexibility facilitates delivery of the stent and radial rigidity is needed to hold open a bodily lumen. The pattern should be designed to maintain the longitudinal flexibility and radial rigidity required of the stent.

A number of techniques have been suggested for the fabrication of stents from tubes and planar films or sheets. One such technique involves laser cutting or etching a pattern onto a material. A pattern may be formed on a planar film or sheet of a material which is then rolled into a tube. Alternatively, a desired pattern may be formed directly onto a tube. Other techniques involve forming a desired pattern into a sheet or a tube via chemical etching or electrical discharge machining. Laser cutting of stents has been described in a number of publications including U.S. Pat. No. 5,780,807 to Saunders, U.S. Pat. No. 5,922,005 to Richter and U.S. Pat. No. 5,906,759 to Richter.

The first step in treatment of a diseased site with a stent is locating a region that may require treatment such as a suspected lesion in a vessel, typically by obtaining an X-Ray image of the vessel. To obtain an image, a contrast agent which contains a radio-opaque substance such as iodine is injected into a vessel. Radio-opaque refers to the ability of a substance to absorb X-Rays. The X-ray image depicts a profile of the vessel from which a physican can identify a potential treatment region. The treatment then involves both delivery and deployment of the stent. "Delivery" refers to introducing and transporting the stent through a bodily lumen to a region in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen. In the case of a balloon expandable stent, the stent is mounted about a balloon disposed on the catheter. Mounting the stent typically involved compressing or crimping the stent onto the balloon. The stent is then expanded by inflating the balloon. The balloon may then be deflated and the catheter withdrawn. In the case of a self-expanding stent, the stent may secured to the catheter via a retractable sheath or a sock. When the stent is in a desired bodily location, the sheath may be withdrawn allowing the stent to self-expand. The stent may be visualized during delivery and deployment using X-Ray imaging if it contains radio-opaque materials. By looking at the position of stent with respect to the treatment region, the stent may be advanced with the catheter to a location. After implantation of the stent additional contrast agent may be injected to obtain an image of the treated vessel. There are several desirable properties for a stent to have that greatly facilitate the delivery, deployment, and treatment of a diseased vessel.

Longitudinal flexibility is important for successful delivery of the stent. In addition, radial strength is vital for holding open a vessel. Also, as the profile of a stent decreases, the easier is its delivery, and the smaller the disruption of blood flow. Additionally, in order to visualize a stent during deployment it is also important for a stent to include at least some radio-opaque materials. Furthermore, it is also desirable for a stent to be bioeroable. Many treatments utilizing stents require the presence of a stent in the vessel for between about six and twelve months. Stents fabricated from biodegradable polymers may be configured to completely erode after the clinical need for them has ended.

Although current biodegradable polymer-fabricated stents, biostable metal stents, bierodable metal stents, and polymer-coated metal stents each have certain advantages, they also possess potential shortcomings. Biodegradable polymer-fabricated stents may be configured to degrade after they are no longer needed and also possess a desired degree of flexibility. However, in order to have adequate mechanical strength, such stents require significantly thicker struts than a metallic stent, which results in a larger profile. Inadequete radial strength may contribute to relatively high incidence of recoil of polymer stents after implantation into vessels. In addition, biodegradable polymers, unlike metals, are not radio-opaque which makes visualization of a stent difficult during delivery and after deployment. Moreover, although biostable metallic stents possess favorable mechanical properties, are radio-opaque, and have smaller profiles than polymer-fabricated stents, they are not bioerodable. Bioerodable metallic stents tend to erode too fast, resulting in complete or nearly complete bioerosion before the end of a treatment time. Therefore, there is a present need for stents that possess more of the favorable properties of polymers and metals.

SUMMARY OF THE INVENTION

The present invention is directed to implantable medical devices, such as stents, and methods of manufacturing such devices that include a metallic region composed of a bioerodable metal and a polymer region composed of a biodegradable polymer contacting the metallic region. The metallic region may erode at a different rate when exposed to bodily fluids than the polymer region when exposed to bodily fluids. In certain embodiments, the polymer region is an outer layer and the metallic region is an inner layer of the device. In some embodiments, the metallic region erodes at a faster rate than the polymer region when exposed to bodily fluids.

Further aspects of the invention are directed to implantable medical devices and methods of manufacturing such devices that include a mixture of a biodegradable polymer and bioerodable metallic particles. In some embodiments, the metallic particles are metallic nanoparticles. In some embodiments, the mixture may be used to coat an implantable medical device. In other embodiments, an implantable medical device may be fabricated from the mixture.

DETAILED DESCRIPTION OF THE INVENTION

Figure 1:
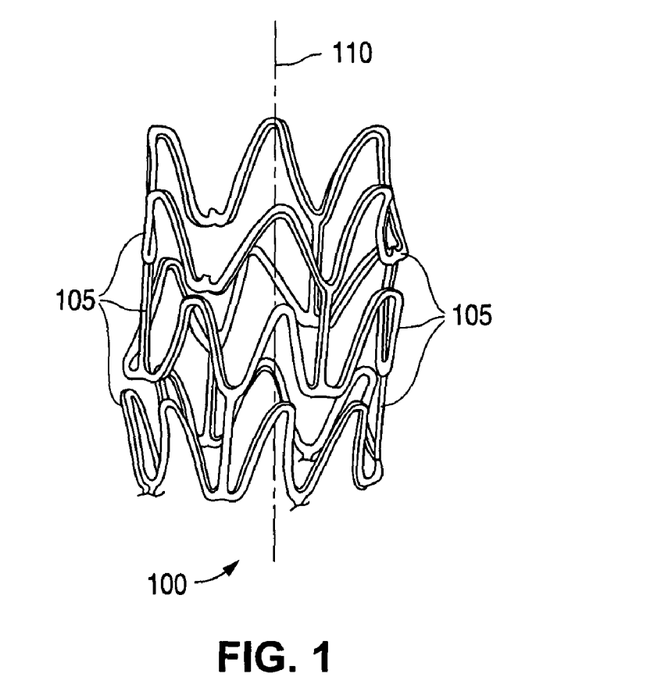
FIG. 1 depicts an example of a stent.

The term "implantable medical device" is intended to include self-expandable stents, balloon-expandable stents, stent-grafts, and grafts. The structural pattern of the device can be of virtually any design. A stent, for example, may include a pattern or network of interconnecting structural elements or struts. FIG. 1 depicts a three-dimensional view of a stent 100 which shows struts 105. The implantable medical device has a cylindrical axis 110. The pattern shown in FIG. 1 should not be limited to what has been illustrated as other stent patterns are easily applicable with the method of the invention. A stent such as stent 100 may be fabricated from a tube by forming a pattern with a technique such as laser cutting or chemical etching.

Various embodiments of the present invention relate to implantable medical devices and methods of manufacturing such devices that possess desired combinations and degrees of properties such as radial strength, flexibility, radio-opacity, low profile or form factor, biodegradability, and drug delivery capability. Implantable medical devices that possess certain desired combinations and degrees of properties may not be fabricated either from polymeric or metallic materials alone. As indicated above, polymeric materials typically are flexible. Also, many biodegradable polymers have erosion rates that make them suitable for treatments that require the presence of a device in a vessel only for a six to twelve month time frame. In addition, metals are radio-opaque and have favorable mechanical properties such as relatively high tensile strength. The embodiments of the present invention involve composite devices and methods of making composite devices that possess desirable properties of polymers and metals to a greater extent than previous composite devices.

For stents made from a biodegradable polymer, the stent may be intended to remain in the body for a duration of time until its intended function of, for example, maintaining vascular patency and/or drug delivery is accomplished. For biodegradable polymers used in coating applications, after the process of degradation, erosion, absorption, and/or resorption has been completed, no polymer will remain on the stent. In some embodiments, very negligible traces or residue may be left behind. The duration is typically in the range of six to twelve months. It is desirable for the stent to provide mechanical support to a vessel for approximately this duration.

Therefore, a preferred erosion profile in such treatments may be slow or minimal degradation for as long as mechanical support for the vessel may be desired. This preferred erosion profile may then include a rapid degradation occurring approximately after the stent is no longer required. A stent configuration that may achieve such a profile may include a slow eroding, flexible outer region and a fast eroding, stiff, strong inner region that provides mechanical support as long as support is desired.

Additionally, it would be also be desirable for such a stent to have a small form factor and radio-opacity. Although biodegradable polymer-fabricated stents are configured to erode, they are not radio-opaque. In addition, in order to have adequate strength, the struts may be significantly thicker than struts in metal stents. For example, a polymer-fabricated stent composed of poly(L-lactic acid) may require struts more than 50% thicker struts than a metallic stent. On the other hand, a metallic stent fabricated from a bioerodable metal, such as magnesium, erodes too quickly to remain intact for the typical treatment time of six to twelve months.

Polymers can be biostable, bioabsorbable, biodegradable, or bioerodable. Biostable refers to polymers that are not biodegradable. The terms biodegradable, bioabsorbable, and bioerodable, as well as degraded, eroded, and absorbed, are used interchangeably and refer to polymers that are capable of being completely eroded or absorbed when exposed to bodily fluids such as blood and can be gradually resorbed, absorbed and/or eliminated by the body.

Biodegradation refers generally to changes in physical and chemical properties that occur in a polymer upon exposure to bodily fluids as in a vascular environment. The changes in properties may include a decrease in molecular weight, deterioration of mechanical properties, and decrease in mass due to erosion or absorption. Mechanical properties may correspond to strength and modulus of the polymer. Deterioration of the mechanical properties of the polymer decreases the ability of a stent, for example, to provide mechanical support in a vessel. The decrease in molecular weight may be caused by, for example, hydrolysis and/or metabolic processes. Hydrolysis is a chemical process in which a molecule is cleaved into two parts by the addition of a molecule of water. Consequently, the degree of degradation of a polymer is strongly dependent on the diffusivity of water in the polymer. A decrease in molecular weight of the polymer can result in deterioration of mechanical properties and contributes to erosion or absorption of the polymer into the bodily fluids. Therefore, the time frame of degradation of a polymer part is dependent on water diffusion, hydrolysis, decrease in molecular weight, and erosion.

Furthermore, polymer erosion spans a continuum from bulk eroding to surface eroding. Bulk eroding refers to degradation of a polymer throughout the bulk of a polymer part exposed to bodily fluids. Alternatively, a polymer may be surface eroding. A surface eroding polymer typically has relatively low water diffusivity. As a result, surface erosion is a heterogeneous process in which degradation and erosion tend to occur at or near a surface of the polymer exposed to the bodily fluids.

Figure 2:
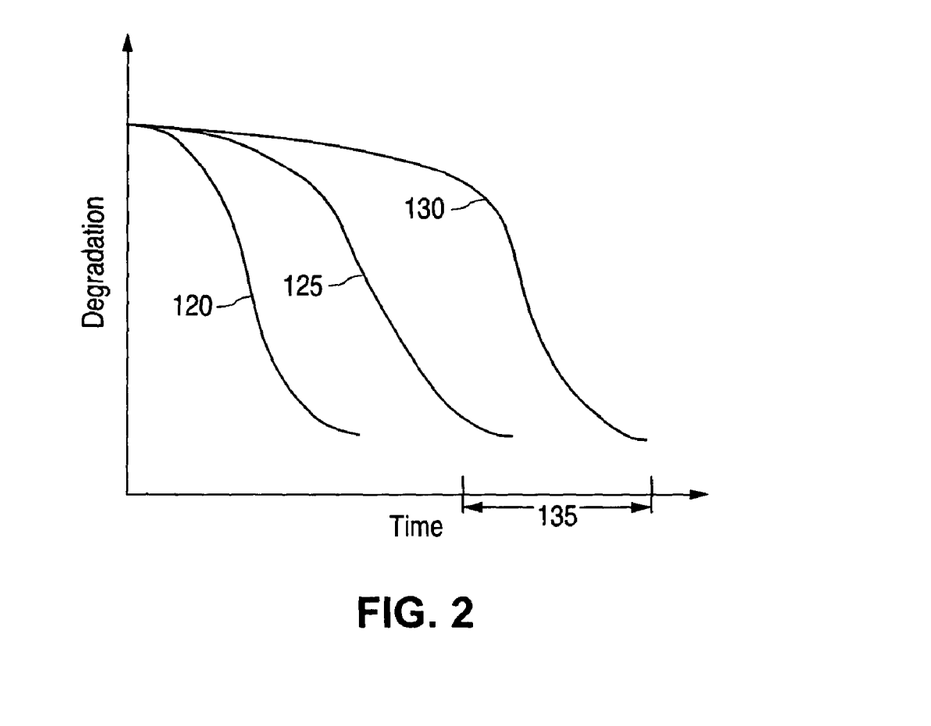
FIGS. 2 and 3 depict degradation as a function of time for a polymer.

Furthermore, the time frame of the degradation of various properties depends on such properties as the diffusivity of water in the polymer and whether the polymer is bulk eroding or surface eroding. For example, for a bulk eroding polymer, the molecular weight loss, deterioration of mechanical properties, and erosion tend to occur sequentially over different time frames. FIG. 2 illustrates degradation as a function of time for a bulk eroding polymer part. A curve 120 represents the decrease in molecular weight that occurs within the bulk of the polymer material. The decrease in molecular weight causes deterioration in mechanical properties of the polymer, which is shown by a curve 125. A curve 130 represents the total erosion of the polymer. Some bulk eroding polymers, may exhibit relatively little erosion even with a substantial loss of molecular weight and deterioration of mechanical properties, as depicted in FIG. 2. For such polymers, much of the erosion may occur over a relatively short time frame, as in a time period 135. Additionally, the water diffusivity in the polymer increases as a bulk-eroding polymer degrades.

Figure 3:
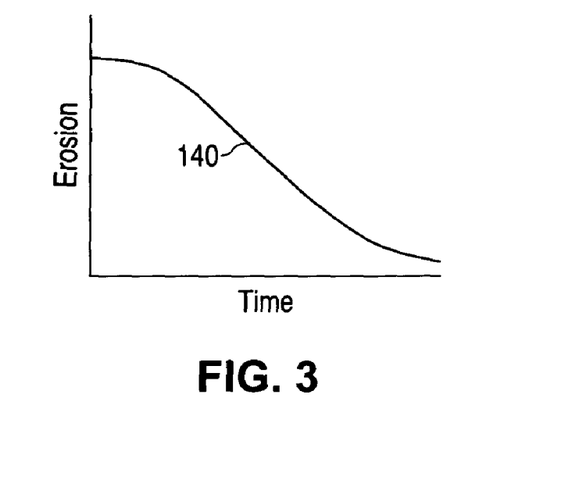

Alternatively, for a surface eroding polymer, changes in the various properties may occur over similar time frames since the degradation is limited to a region at or near an exposed surface. In FIG. 3, a curve 140 depicts the total erosion as a function of time for a surface-eroding polymer part. The erosion rate is substantially dependent on the surface area of a part. Since degradation is heterogeneous, the decrease in molecular weight and deterioration of the mechanical properties occur at or near the surface of a surface-eroding polymer part. In the bulk or away from the surface of a surface-eroding polymer part, the molecular weight and mechanical properties are unchanged or substantially unchanged.

Representative examples of polymers that may be used to fabricate an implantable medical device using the methods disclosed herein include, but are not limited to, poly(N-acetylglucosamine) (Chitin), Chitoson, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially well suited for use in fabricating an implantable medical device according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

Additionally, some metals are considered bioerodable since they tend to erode or corrode relatively rapidly when exposed to bodily fluids. Biostable metals refer to metals that are not bioerodable. Biostable metals have negligible erosion or corrosion rates when exposed to bodily fluids. In general, metal erosion or corrosion involves a chemical reaction between a metal surface and its environment. Erosion or corrosion in a wet environment, such as a vascular environment, results in removal of metal atoms from the metal surface. The metal atoms at the surface lose electrons and become actively charged ions that leave the metal to form salts in solution. A bioerodable stent suitable for use as a stent material forms erosion products that do not negatively impact bodily functions. Representative examples of biodegradable metals that may be used to fabricate an implantable medical device may include, but are not limited to, magnesium, zinc, and iron. In one embodiment, a bioerodable metal stent may be completely eroded when exposed to bodily fluids, such as blood, between about a week and about three months, or more narrowly, between about one month and about two months.

In general, it may be desirable to manufacture an implantable medical that includes relatively distinct regions that have different erosion profiles when exposed to bodily fluids. In this way the erosion profile of the stent may be customized to various treatments. Various embodiments of an implantable medical device with such erosion profiles may include a metallic region composed of a bioerodable metal and a polymer region composed of a biodegradable polymer. The metallic region may erode at a different rate when exposed to bodily fluids than the polymer region when exposed to bodily fluids. In some embodiments, the polymer region may be an outer region or layer of the device and the metallic region may be an inner region or layer of the device. An outer region or layer may refer to a region or layer that is exposed first to a vascular environment. Direct contact or exposure of the inner region or layer to a vascular environment may be inhibited or prevented by an outer region or a region that is closer to the vascular environment. For example, a strut of a stent may include an inner region or core with an outer region or coating that inhibits or prevents direct contact or exposure of the inner region or core to a vascular environment. The metallic region may be configured to provide mechanical support for at least some of the time the device is implanted in a bodily lumen.

In certain embodiments, the implantable medical device may include a metallic region that includes a cylindrical or substantially cylindrical cross-sectional pattern of struts. The strut pattern can also be square, rectangular, oval, or another cross-sectional shape. For example, the metallic region may be a cylindrical or substantially cylindrical coil or mesh of metallic wire. In addition, a metallic region may be a pattern of struts formed on a metallic tube by cutting or etching. The polymer region may be a biodegradable polymer coating on the metallic region. In some embodiments, the polymer region may include an active agent. The polymer region may be configured to release the active agent for a selected amount of time. The release may occur through the brake-up of the polymer and/or via migration of the active agent out of the polymer. The selected amount of time may correspond approximately to a desired treatment time of a stent. Additionally, the metallic region may have pores that are configured to include an active agent. For example, the metallic region can be formed by sintering particles, fibers, and wires of material.

In some embodiments, the metallic region may erode at a faster rate when exposed to bodily fluids than the polymer region when exposed to bodily fluids. In some embodiments, the polymer region may be configured to delay, inhibit, or prevent erosion of the metallic region in a manner that allows the metallic region to provide mechanical support to a bodily lumen. For example, the polymer region may be configured to delay, inhibit, or prevent erosion of the metallic region for a selected time period. The selected time period may be at least a portion of the time period that the metallic region is desired to provide mechanical support. It may be desirable for a metallic region to provide mechanical support for a majority of, all of, or longer than a desired treatment time of the stent.

Some embodiments may include a metallic region that is configured to erode when the metallic region is exposed to bodily fluids due to degradation of the polymer region. The metallic region may be exposed to bodily fluids by erosion of the polymer region and/or diffusion of bodily fluids through the polymer region. In some embodiments, a metal region may start to erode when the polymer region is only partially degraded and/or eroded. Partially means less than 50% of the polymer, or alternatively less than 40%, 30%, 20%, 10%, or 5%. In other embodiments, the metal region may start to erode when the polymer region is completely (greater than 99%) degraded and/or eroded or when a majority of the polymer is degraded and/or eroded. Majority includes over 50%, 60%, 70%, 80%, 90%, or alternatively, over 95% of the polymer.

In some embodiments, an outer polymer region may be a bulk eroding polymer. Representative examples of bulk eroding polymers include, but are not limited to, poly(L-lactide), poly(glycolide), poly(D,L-lactide), poly(trimethylene carbonate), polycaprolactone, and copolymers thereof. During a treatment time, the polymer degrades resulting in a decrease in the molecular weight of the polymer region and deterioration of mechanical properties. A polymer may be selected that has a relatively low water diffusivity. In some embodiments, the polymer may be capable of absorbing less than about 3% by volume, or more narrowly, less than about 1% of its volume. However, water diffusivity in the polymer increases as the polymer region degrades. The increased diffusivity of water may result in erosion of the metallic region prior to complete erosion of the polymer region. In an embodiment, the metallic region may be configured to completely or almost completely erode before the polymer region is completely eroded. In other embodiments, the polymer region may be configured to completely or almost completely erode before the metallic region is completely eroded.

In other embodiments, an outer polymer region may be a surface eroding polymer. Representative examples of surface eroding polymers include, but are not limited to, polyorthoesters, polyanhydrides and copolymers thereof. A surface eroding polymer may be selected that has a water diffusivity that inhibits or prevents erosion of the metallic region for a selected time period. The metallic region may be configured to erode when erosion of the polymer region exposes a portion of the metallic region to bodily fluids. Due to higher water diffusivity in a bulk eroding polymer, it is expected that the erosion of the metallic region will occur later and over a smaller time frame with a surface eroding polymer as an outer region than with a bulk eroding polymer as an outer region.

Figure 4:
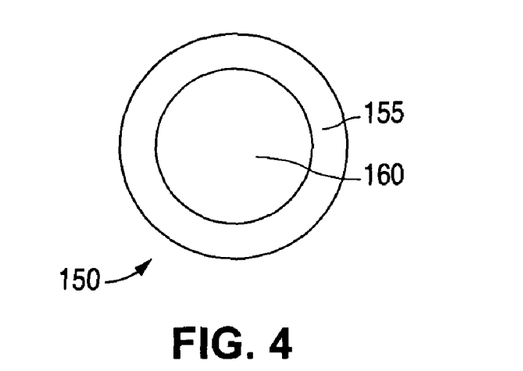
FIG. 4 depicts a schematic illustration of a cross-section of a strut.
Figure 5A:
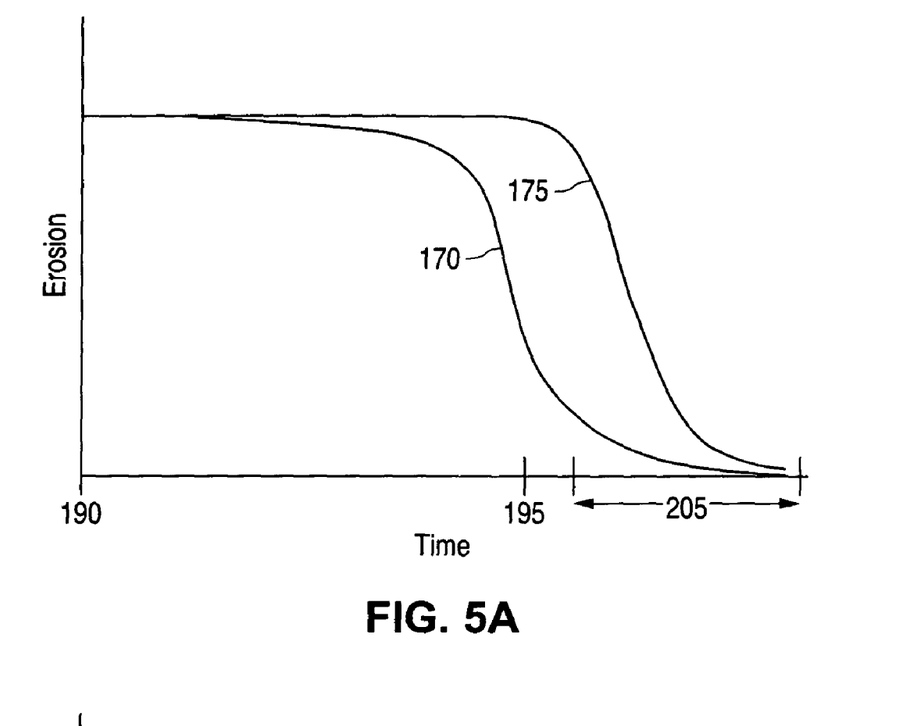
FIGS. 5A and 5B depict erosion profiles of a stent.
Figure 5B:
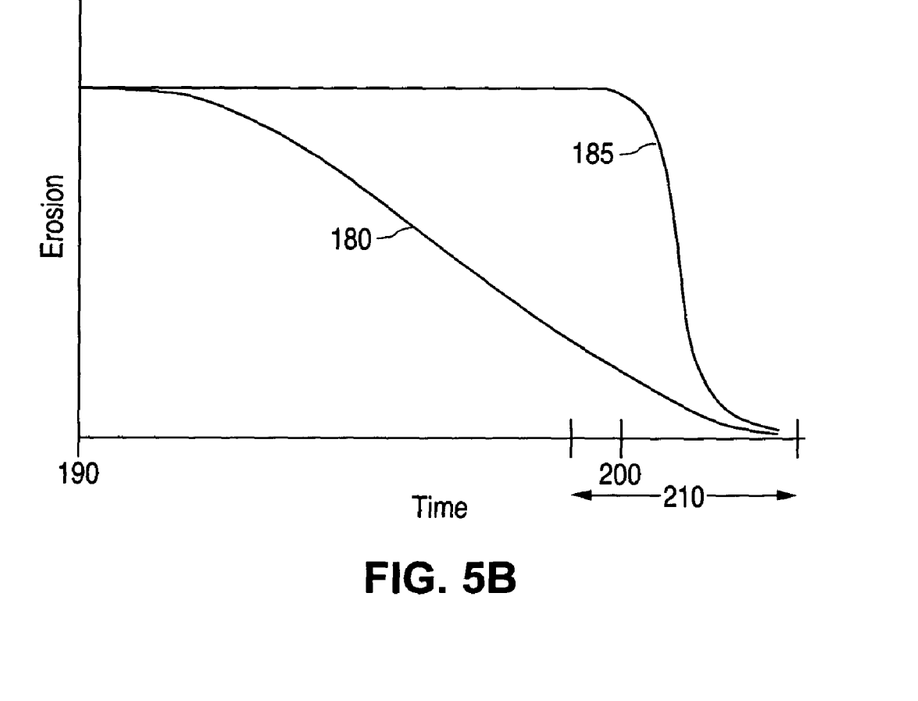

FIG. 4 depicts a schematic illustration of an embodiment of a cross-section of a strut 150 of a stent that includes an outer region 155 and an inner region 160. Outer region 155 is a relatively slow eroding polymer region and inner region 160 is a relatively fast eroding metallic region. FIGS. 5A and 5B illustrate examples of erosion as a function of time for such a stent with an outer biodegradable polymer region and an inner bioerodable metallic inner region. FIG. 5A depicts erosion for a stent with a bulk eroding polymer region and FIG. 5B depicts erosion for a stent with a surface eroding polymer region. In FIG. 5A, a curve 170 represents the total erosion of the polymer region and curve 175 represents the total erosion of the inner metallic region. In FIG. 5B, a curve 180 represents the total erosion of the polymer region a curve 185 represents the total erosion of the metallic region. A time 190 corresponds to an approximate time of implantation of the stent in a vessel. From time 190 to approximately a time 195 in FIG. 5A and between time 190 and approximately time 200 in FIG. 5B, there is minimal erosion of the metallic region. At some time during a time period 205 in FIG. 5A and a time period 210 in FIG. 5B, the stent may be no longer required for treatment. During time periods 205 and 210, the polymer and metallic regions may be completely or almost completely eroded and the metallic regions may no longer provide mechanical support. The erosion of the metallic region rises sharply during time periods 205 and 210 due to degradation and/or erosion of the polymer regions. A comparison of curve 175 to curve 185 illustrates the sharper erosion profile of the metallic region when a surface eroding polymer is used rather than bulk eroding polymer for the polymer region.

In certain embodiments, the device may have more desirable properties than a polymer-fabricated device; a biostable or bioerodable metal device; or a polymer-coated biostable metal device. For instance, the device may have a greater radial strength than an equivalent device fabricated from the biodegradable polymer in which the equivalent device has the same structure and dimensions as the device. Dimensions may include the length and radius of a stent and cross-sectional dimensions of struts of the stent. Structure may include the structure of a pattern of a stent. In addition, the device may have greater flexibility than an equivalent device fabricated from the metal in which the equivalent device has the same dimensions and structure as the device. Additionally, the device may include a stent with a smaller profile than an equivalent device fabricated from the biodegradable polymer. An equivalent device is an equivalent stent with the same radial strength and same dimensions and structure as the device. A smaller profile may correspond to thinner struts. Also, the device may have sufficient radio-opacity to be imaged by X-Ray radiation, unlike a polymer-fabricated device. Also, as discussed above, the device may also be capable of completely eroding away when it is no longer required for treatment.

In certain embodiments, the metallic region and the polymer region may be configured to have certain desired properties such as erosion rate and mechanical properties. Desired properties may be obtained by forming the polymer region and/or the metallic region from polymers and/or metals, respectively, to obtain the desired properties. The polymer may have a uniform or substantially uniform composition and uniform or substantially uniform properties such as erosion rate and mechanical properties. The polymer region may be a pure or a substantially pure biodegradable polymer. Alternatively, the polymer may be a uniform or substantially uniform mixture of at least two types of polymers. Similarly, the metallic region may have a uniform or substantially, uniform composition and uniform or substantially uniform properties such as erosion rate and mechanical properties. The metal may a pure or substantially pure metal. Also, the metal region may be a uniform or substantially uniform alloy that includes at least two types of metals. In addition, the metal region may be a uniform or substantially uniform mixture that includes at least two types of metals. The properties such as erosion rate may be uniform or substantially uniform.

Figure 6:
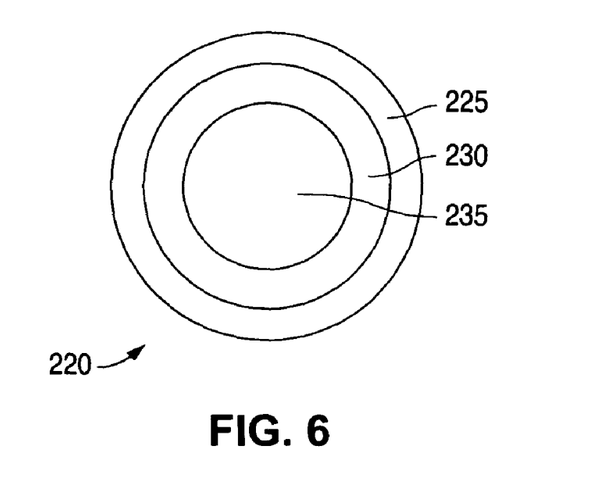
FIG. 6 depicts a schematic illustration of a cross-section of a strut.

Alternatively, it may be desirable in other embodiments to have a polymer region and/or metallic region that have non-uniform composition with nonuniform properties. In some embodiments, the polymer region may be a nonuniform mixture of at least two types of polymers. Similarly, the metallic region may be a nonuniform mixture of at least two types of metals. In other embodiments, the polymer region may include at least two uniform or substantially uniform layers in which at least two layers have different erosion rates. Different layers may correspond to different pure or substantially pure polymers or polymer mixtures. In some embodiments, one layer may be a bulk eroding polymer and another layer may be a surface eroding polymer. In one embodiment, the surface eroding polymer can be disposed over the bulk eroding polymer. Alternatively, the bulk eroding polymer can be disposed over the surface eroding polymer. In a similar manner, the metallic region may include at least two layers in which at least two layers have different erosion rates. Thus, the erosion and erosion rate may be customized to any number of treatment applications. For example, FIG. 6 depicts a schematic illustration of a cross-section of strut 220. Strut 220 in FIG. 6 may have a polymer region that includes a polymer layer 225, a polymer layer 230, and a metallic region 235. In addition, strut 220 in FIG. 6 may have a metallic region that includes a metallic layer 230, a metallic layer 235, and a polymer region 225.

In other embodiments, the properties such as the erosion rate of a stent may be further customized by forming a stent with at least three alternating polymer and metallic regions. In one embodiment, a second metallic region may be formed that contacts the polymer region in which the polymer region is between the metallic region and the second metallic region. Additionally, another embodiment may include forming a second polymer region that contacts the metallic region in which metallic region is between the polymer region and the second polymer region. In some embodiments, one or more of the polymer regions may include an active agent. In other embodiments, one or more of the metallic regions may include an active agent. For example, strut 220 in FIG. 6 may have a polymer region 225, a polymer region 235, and a metallic region 230 between the polymer regions. In addition, strut 220 in FIG. 6 may have a polymer region 230, a metallic region 235, and a metallic region 225. A polymer region may be biostable or biodegradable. Similarly, a metallic region may be biostable or biodegradable. Preferably, one or all of the polymeric regions are biodegradable and one or all of the metallic regions are degradable as well.

Further embodiments of incorporating desirable properties into implantable medical devices may include a device that is at least partially composed of a material that is a mixture of a biodegradable polymer and bioerodable metallic material. In some embodiments, an implantable medical device may be composed of a mixture having a biodegradable polymer and bioerodable metallic particles. In an embodiment, a method of manufacturing the device may include mixing a biodegradable polymer and bioerodable metallic particles to form the mixture. In certain embodiments, the biodegradable polymer and the bioerodable metallic particles may be mixed in a mixing apparatus such as an extruder. Certain embodiments may further include mixing a biostable polymer and/or biostable metallic particles with the biodegradable polymer and bioerodable metallic particles. Other embodiments may further include mixing the biodegradable polymer and bioerodable metallic particles with metallic particles that include at least one particle composed of a mixture or alloy of at least of one bioerodable metal and at least one biostable metal. Some embodiments of the method may further include using the mixture to fabricate an implantable medical device or to coat an implantable medical device.

In certain embodiments, the metallic particles may be metallic nanoparticles. A "nanoparticle" refers to a particle with a dimension in the range of about 1 nm to about 10,000 nm. A significant advantage of nanoparticles over larger particles is that nanoparticles may form a more uniform mixture in a polymer matrix. A resulting mixture may then have a more uniform improvement of properties such a radial strength and flexibility. Additionally, nanoparticles may be absorbed by bodily fluids such as blood without negative impact to bodily functions. Representative examples of metallic particles may include magnesium, zinc, aluminum, and oxides of such metals. In some embodiments, the mixture may also include an active agent. In other embodiments, the nanoparticles can include an active agent or a drug.

The biodegradable polymer may be a pure or substantially pure biodegradable polymer. Alternatively, the biodegradable polymer may be a mixture of at least two types of biodegradable polymers. A metallic particle may be a pure or substantially pure bioerodable metal or bieoerodable metal compound. Alternatively, a metallic particle may be a mixture of at least two types of bioerodable metals or bioerodable metallic compounds. A metallic particle may also be an alloy composed of at least two types of bioerodable metals. The metallic particles may be a mixture of at least two types of metallic particles.

In certain embodiments, an implantable medical device manufactured from the mixture including a biodegradable polymer and bioerodable metallic particles may be configured to have desired properties. A desired property may include, but is not limited to, a desired erosion rate, a desired degree of radio-opacity, or desired mechanical performance, for example, a desired radial strength. In some embodiments, desired properties of a device may be obtained by modifying the composition of the mixture of the biodegradable polymer and bioerodable metallic particles. In one embodiment, the composition of the biodegradable polymer may be modified. Differences in erosion rates and/or mechanical performance of different biodegradable polymers may be used to obtain desired properties of the mixture.

Similarly, the composition of the mixture may be modified by modifying the composition of the metallic particles. For example, the ratio or concentration of different types of metallic particles in the mixture or the composition of individual particles may be altered to obtain desired properties.

In other embodiments, the ratio of polymer to metallic particles or metal may also be modified. Since a polymer and metallic particles may have different erosion rates, the ratio of polymer to metallic particles may be modified to obtain a desired erosion rate. For example, if a bioerodable metal has a faster erosion rate than the biodegradable polymer, decreasing the ratio of polymer to metallic particles may increase the erosion rate of a device. Additionally, the radial strength of a device may be increased by decreasing the ratio of polymer to metallic particles.

Several embodiments may include various ways of using the mixture to fabricate or to coat an implantable medical device. In an embodiment, fabricating a device may include forming a tube from the mixture. A tube may be formed from the mixture using an extruder. Alternatively, a planar film or sheet may be formed from the mixture, also through extrusion. A tube may then be formed from the planar film or sheet by rolling and bonding the film or sheet. In an embodiment, a stent pattern of struts, such as the one pictured in FIG. 1, may be formed on the tube. The pattern may be formed by a technique such as laser cutting or chemical etching. Examples of lasers that may be used for cutting stent patterns include, but are not limited to, excimer, $CO_2$, or YAG. In another embodiment, fibers may be formed from the polymer and metallic particle mixture and formed into a stent.

In other embodiments, the mixture may be used to coat an implantable medical device with the mixture. The device to be coated may be a polymer-fabricated stent; a metallic stent; or a stent fabricated from polymer and metallic particles. In some embodiments, a stent coated by the mixture may be completely or almost completely bioerodable. The mixture for use as a coating may be composed of a biodegradable polymer and a bioerodable metal. In one embodiment, the substrate stent may be a polymer-fabricated stent composed of a biodegradable polymer. In another embodiment, the substrate stent may be a metallic stent that is composed of a bioerodable metal. Other embodiments may include coating a stent fabricated from a mixture of biodegradable polymer and bioerodable metallic particles.

In certain embodiments, a device fabricated or coated with a polymer and metallic particle mixture may have more desirable properties than a polymer-fabricated device, a metallic device, or a polymer-coated metal device. A device fabricated from the mixture of polymer and metallic particles may have greater radial strength and greater flexibility than an equivalent device fabricated from the polymer. An equivalent device is the same dimensions and structure as the device. Moreover, a device manufactured with a polymer and metallic particle mixture may be a stent with a smaller profile than an equivalent stent fabricated from the polymer. A smaller profile may include thinner struts. The equivalent device is an equivalent stent with the same radial strength and the same dimensions and structure as the device. Furthermore, due to the metallic particles, the device may have sufficient radio-opacity to be imaged by X-Ray radiation.

In addition, the composition of metallic particles in the mixture may be modified to obtain desired properties of the device. For example, the composition may be modified to obtain a desired degree of radio-opacity and mechanical behavior such as radial strength and/or flexibility.

Additionally, cutting stent patterns on polymer parts can be difficult since many polymers absorb little or no energy from laser light emitted by lasers conventionally used for cutting patterns. However, the metallic particles in the polymer and metallic particle mixture may help to overcome this difficulty by increasing the absorption of energy from the laser light.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent for implanting in a vascular lumen, comprising a stent body that is expandable from a pre-implant configuration to a post-implant configuration inside the vascular lumen, the stent body including a strut having a cross-section, wherein the cross-section of the strut including:

a metallic region comprising a bioerodable metal; wherein the bioerodable metal comprises a pure or substantially pure bioerodable metal; and a polymer region comprising a biodegradable polymer contacting and disposed over the metallic region, wherein the metallic region erodes at a different rate when exposed to bodily fluids than the polymer region when exposed to bodily fluids, and wherein the metallic region starts to erode when the polymer region is at least partially degraded after the stent body has been expanded to the post-implant configuration inside the vascular lumen, wherein the bioerodable metal erodes at a faster rate when exposed to bodily fluids than the biodegradable polymer when exposed to bodily fluids, wherein the metallic region is configured to completely or almost completely erode before the polymer region is completely or almost completely eroded.

2. The stent of claim 1, wherein the polymer comprises at least one material selected from the group consisting of poly (hydroxyvalerate), poly(lactide-co-glycolide), poly(hydroxybutyrate), poly(hydroxybutyrate-co-valerate), polyorthoester, polyanhydride, poly(glycolic acid), poly (glycolide), poly(L-lactic acid), poly(L-lactide), poly(D,L-lactic acid), poly(D,L-lactide), poly(caprolactone), poly (trimethylene carbonate), and polyester amide.

3. The stent of claim 1, wherein the bioerodable metal is selected from the group consisting of magnesium, zinc, and iron.

4. The stent of claim 1, wherein the biodegradable polymer comprises a pure or substantially pure biodegradable polymer.

5. The stent of claim 1, wherein the biodegradable polymer comprises a mixture of at least two types of biodegradable polymers.

6. The stent of claim 1, wherein the biodegradable polymer comprises a bulk eroding polymer.

7. The stent of claim 1, wherein the biodegradable polymer comprises a surface eroding polymer.

8. The stent of claim 1, wherein the bioerodable metal comprises a mixture comprising at least two types of metals.

9. The stent of claim 1, wherein the bioerodable metal comprises an alloy comprising at least two types of metals.

10. The stent of claim 1, wherein the polymer region comprises an active agent.

11. The stent of claim 1, wherein the metallic region comprises pores comprising an active agent.

12. The stent of claim 1, wherein the polymer region is configured to release an active agent.

13. The stent of claim 1, wherein the polymer region is configured to delay, inhibit, or prevent erosion of the metallic region.

14. The stent of claim 1, wherein the polymer region is configured to inhibit or prevent erosion of the metallic region in a manner that allows the metallic region to provide mechanical support to a bodily lumen.

15. The stent of claim 1, wherein the polymer region is configured to inhibit or prevent erosion of the metallic region for at least a portion of, all of, or longer than the time period that the metallic region is desired to provide mechanical support of a bodily lumen.

16. The stent of claim 1, wherein the stent comprises sufficient radio-opacity to be imaged by X-Ray radiation.

17. The stent of claim 1, wherein the metallic region comprises a cylindrical or substantially cylindrical coil or mesh of metallic wire.

18. The stent of claim 1, wherein the metallic region comprises a cylindrical pattern of struts.

19. The stent of claim 1, wherein the polymer region comprises a coating comprising the biodegradable polymer on the metallic region.

20. The stent of claim 1, wherein the polymer region comprises uniform or substantially uniform erosion rate.

21. The stent of claim 1, wherein the metallic region comprises a uniform or substantially uniform composition and uniform or substantially uniform erosion rate.

22. The stent of claim 1, wherein the polymer region comprises at least two layers, wherein at least two layers comprise different erosion rates.

23. The stent of claim 1, wherein the metallic region comprises at least two layers, wherein at least two layers comprise different erosion rates.

24. The stent of claim 1, further comprising a second metallic region contacting the polymer region, wherein the polymer region is between the metallic region and the second metallic region.

25. The stent of claim 1, wherein the polymer region inhibits or prevents direct contact or exposure of the metallic region to a vascular environment.

26. The stent of claim 1, wherein the polymer region completely covers inward-facing surfaces and outward-facing surfaces of the stent.

27. The stent of claim 1, wherein the bioerodable metal is magnesium.

* * * * *